(12) United States Patent
Masquelier (10) Patent No.: US 6,688,187 B1
(45) Date of Patent: Feb. 10, 2004

(54) AEROSOL SAMPLING SYSTEM (75) Inventor: Donald A. Masquelier, Tracy, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/454,661

(22) Filed: Jun. 3, 2003

Related U.S. Application Data (60) Provisional application No. 60/409,621, filed on Sep. 10, 2002.

(51) Int. Cl.[7] ................................................. G01N 1/00
(52) U.S. Cl. ................................................. 73/863.22
(58) Field of Search ........................ 73/863.21, 863.22, 73/864.81, 28.04–28.06, 28.01; 96/269–271, 413, 360; 435/30, 34; 95/267, 269, 271; 55/437, 438, 406

(56) References Cited

U.S. PATENT DOCUMENTS

| | | | |
|---|---|---|---|
| 4,461,183 A | * | 7/1984 | Wedding |
| 5,040,424 A | | 8/1991 | Marple et al. |
| 5,183,481 A | | 2/1993 | Felder |
| 5,412,975 A | * | 5/1995 | Raabe et al. |
| 5,425,802 A | | 6/1995 | Burton et al. |
| 6,402,817 B1 | | 6/2002 | Bergman |
| 6,484,594 B1 | | 11/2002 | Saaski et al. |
| 6,520,034 B1 | | 2/2003 | Masquelier et al. |
| 6,532,835 B1 | | 3/2003 | Saaski et al. |

* cited by examiner

*Primary Examiner*—Robert Raevis
(74) *Attorney, Agent, or Firm*—Eddie E. Scott; Alan H. Thompson (57) ABSTRACT

A system for sampling air and collecting particulate of a predetermined particle size range. A low pass section has an opening of a preselected size for gathering the air but excluding particles larger than the sample particles. An impactor section is connected to the low pass section and separates the air flow into a bypass air flow that does not contain the sample particles and a product air flow that does contain the sample particles. A wetted-wall cyclone collector, connected to the impactor section, receives the product air flow and traps the sample particles in a liquid.

10 Claims, 6 Drawing Sheets

AEROSOL SAMPLING SYSTEM

CROSS-REFERENCE TO RELATED APPLICATIONS

This application claims the benefit of U.S. Provisional Patent Application No. 60/409,621 filed Sep. 10, 2002 titled "High Collection Rate Aerosol Sampling System (HiCRASS)." U.S. Provisional Patent Application No. 60/409,621 filed Sep. 10, 2002 titled, "High Collection Rate Aerosol Sampling System (HiCRASS)" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to sampling and more particularly to aerosol sampling.

2. State of Technology

U.S. Pat. No. 5,040,424 to Virgil A. Maple, et al patented Aug. 20, 1991 and assigned to Regents of the University of Minnesota provides the following state of technology information, "In recent years the Environmental Protection Agency (EPA) has established that a particle separating inlet which removes all of the particles that are larger than 10 microns from the flow before collecting the particles for analyzers should be developed. The sampling characteristics for such inlet must be substantially insensitive to wind direction and wind speed. The Federal Register, Volume 49, No. 55 for Tuesday Mar. 20, 1984 contains the proposed rules for testing such sampler inlet."

U.S. Pat. No. 5,183,481 to William Felder patented Feb. 2, 1993 and assigned to Aerochem Research Laboratories provides the following state of technology information, "The separation and collection of fine particles from gases is of intense interest in material sciences where fine particles may have unique and valuable properties. Often such particles are produced along with byproduct vapors in high temperature environments. It is frequently of importance to preserve the purity of the particles by separating them from the byproduct vapors which may condense on them if the particles are simply filtered. The separation and collection of fine particles from gases is also important in preventing such particles from entering the atmosphere as an unintended consequence of manufacturing or power generation processes, as in the manufacture of cements and the fly ash produced from coal-fired electrical generators. Large investments are made in filtration systems and/or high voltage electrical devices to separate and collect the fine particles that can cause pollution. The separation and collection of fine particles from gases is also important in research on atmospheric aerosols and particulates and in preparing powders comprising particles of uniform size for such applications as advanced materials processing."

U.S. Pat. No. 5,425,802 to Robert M. Burton et al patented Jun. 20, 1995 and assigned to The United States of America as represented by the Administrator of Environmental Protection Agency President and Fellows of Harvard provides the following state of technology information, "Particle classification according to aerodynamic size can be carried out with a number of different devices, including elutriators, cyclones, centrifuges and impactors. Inertial impactors have been widely used for particle collection, mainly because of their sharp cut-off characteristics."

U.S. Pat. No. 6,402,817 to Warner Bergman patented Jun. 11, 2002 and assigned to The Regents of the University of California provides the following state of technology information, "Impactors belong to a class of instruments called inertial classifiers, which separate particles in a fluid stream based on the inertia of particles. In general these instruments operate by forcing a change in the direction of the fluid stream containing the particles. Because of the particles inertia the particles cannot follow the fluid stream. If an obstacle is placed in the path of the fluid stream, the fluid is deflected around the obstacle while the particles are less able to deflect around the obstacle. If the particle inertia exceeds a minimum quantity, the particle cannot deflect around the obstacle and will be caught by the obstacle."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an environmental sampling system for sampling air and collecting sample particles of a predetermined particle size range from the air. A low pass section has an opening for gathering the air. The opening excludes particles larger than the desired sample particle size. The low pass section produces a total air flow that contains the sample particles. An impactor section is connected to the low pass section and receives the total air flow. The impactor section separates the total air flow into a bypass air flow that excludes particles smaller than the desired size range and a product air flow containing the sample particles. A wetted-wall cyclone collector is connected to the impactor section and receives the product air flow. The wetted-wall cyclone collector traps the sample particles of a predetermined particle size range are concentrated in the liquid.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 1 shows the upper section of one specific embodiment of the invention.

FIG. 2 is an illustration that shows the cap section limiting the larger particulate size range entering the collector.

DETAILED DESCRIPTION OF THE INVENTION

As the threat of biological weapons (BW) increases, both in military theaters and civilian populations, the need for complete systems for the rapid detection and analysis of pathogenic organisms becomes increasingly important. The first step in any system for detection and characterization of biological agents is a sample collector. This can take on the simple form of a cotton swab for solid surfaces, or as in the case of airborne pathogens, an aerosol sample collector is used to collect and concentrate airborne particulate into a liquid sample volume for subsequent preparation and analysis. An aerosol sampler is the most appropriate for continuous monitoring scenarios, where repeated swabbing of settled particles is impractical.

Aerosol sampling systems also have use in medical facilities and research and development facilities. There are a variety of medical applications where monitoring for biological pathogens would be useful. A good example of this is monitoring in hospitals and clinics for highly infectious agents such as tuberculosis or nosocomial diseases that can threaten the well being of patients and health care professionals. Aerosol sampling systems also have use in environmental monitoring, that is any application that would benefit from environmental monitoring of biological species. One example is continuous aerosol monitoring of bacterial and other pathogens that could affect the health of livestock (such as the recent hoof and mouth disease outbreak).

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
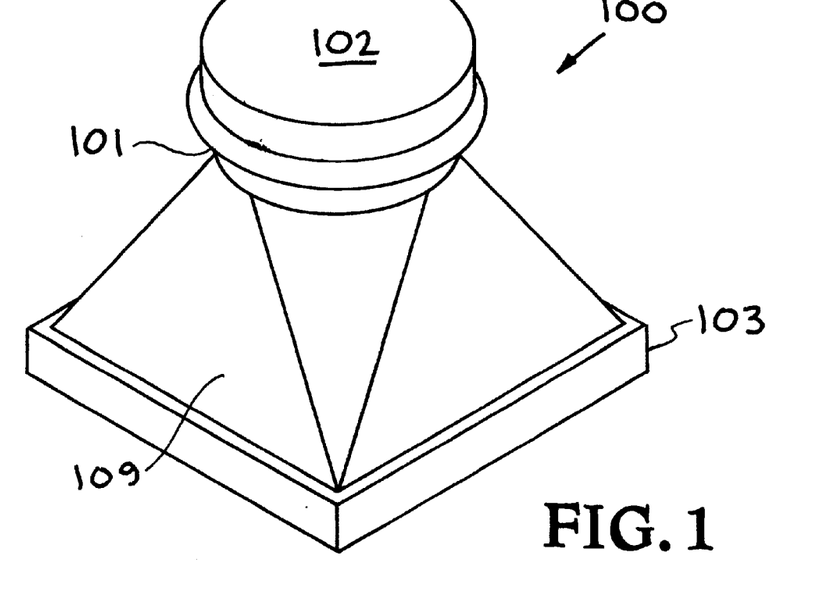

The upper portion of one specific embodiment of the invention is shown in FIG. 1. The specific embodiment is designated generally by the reference numeral 100. The system 100 provides a compact, high collection rate aerosol sampling system. The system 100 is particularly useful with the latest generation of Biological Warfare agent detection systems. An air sampling system is a critical component in integrated biological warfare detection system. The system 100 also has use in medical facilities and research and development facilities.

In the system 100 a very high volume flow of aerosol particles is drawn into an annular slot 101 formed in a cap 102 that is designed to only allow the passage of particles smaller than a pre-set size. The pre-set size can be selected as desired. A specific example of an embodiment of the system 100, a very high volume flow of aerosol particles (e.g., up to 3313 Lpm) is drawn into an annular slot 101 formed in a cap 102 that is designed to only allow the passage of particles smaller than 10 microns. The accepted particles continue on into a dichotomous virtual impaction section 103 that returns all the aerosol particles smaller than 1-micron back into the environment. The remaining particles, (1–10 microns) known as the product, flow into a multi-stage, wetted-wall cyclone collection section. In this stage of the sampling system the product particles are trapped and concentrated into a liquid, typically water, in a volume between 2 and 7 cc. An on-board computer monitors and controls the flow of air through the system using built in hot wire anemometers, as well as controlling the liquid level in the cyclone. At a selected time the computer will stop the flow of air and turn on a built-in peristaltic pump to deliver the sample via an external liquid sample port.

The system 100 has the capability to measure particle sizes in the sampling environment via a built in particle counter with four size ranges, and can store and display the results in real-time. The system is entirely self-contained requiring only a 110 vac power connection. The on-board computer has high-speed communications capability allowing networks of these sampling systems to be remotely operated.

The system 100 is useful for most environmental sampling. It is particularly useful with biological material collection, but can be used for collecting any airborne matter. The system 100 can be used to sample air quality in public buildings such as convention centers and sports arenas, for sampling in food processing facilities, sampling animal pens (such as poultry houses), or for use in monitoring orchards or agricultural areas for the presence of pollens or pesticides. Because of it's relatively compact size and weight it can be used to sample in confined spaces such as found in aircraft or subway systems.

Figure 2:
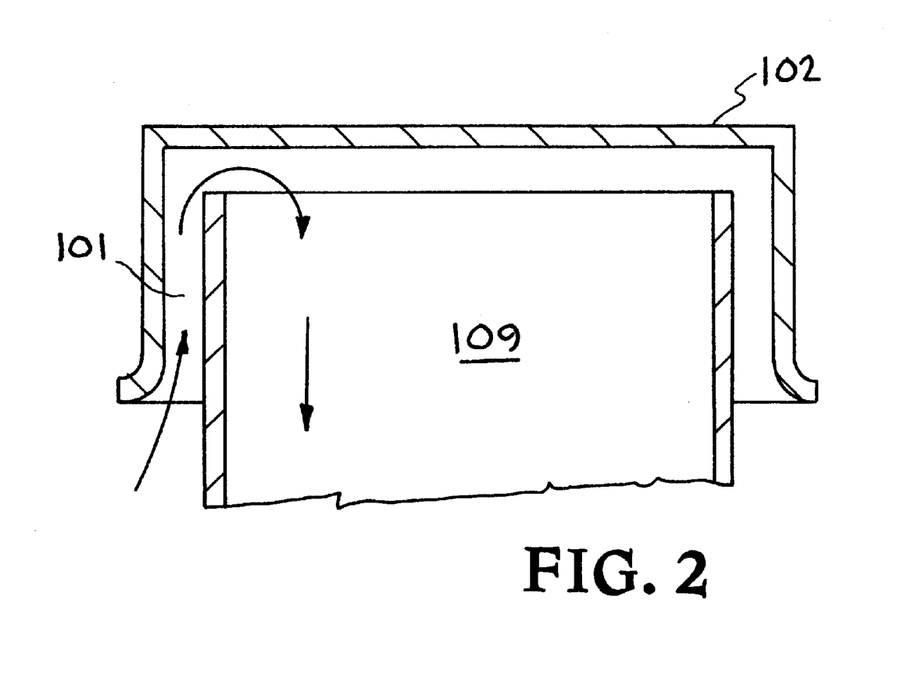

Referring now to FIG. 2, a high volume flow of aerosol particles (e.g., up to 3313 Lpm) is drawn into the annular slot 101 formed in the cap 102. The cap and annular slot 101 are designed to limit the upper or larger particulate size range as they enter the collector. To efficiently pass the smaller particulate, the cap 102 is a "passive" device in that has no moving parts and uses the fact that particulate with a finite mass and moving in a flowstream (in this case air) will not follow the streamlines exactly due to their inertia. If the curvature of a streamline is sufficiently large and the mass of the particulate is correspondingly high, the particle deviates far enough from the streamline to impact with a surface. The particles are drawn into the annular slot 101 and directed into the transition section 109.

Figure 3:
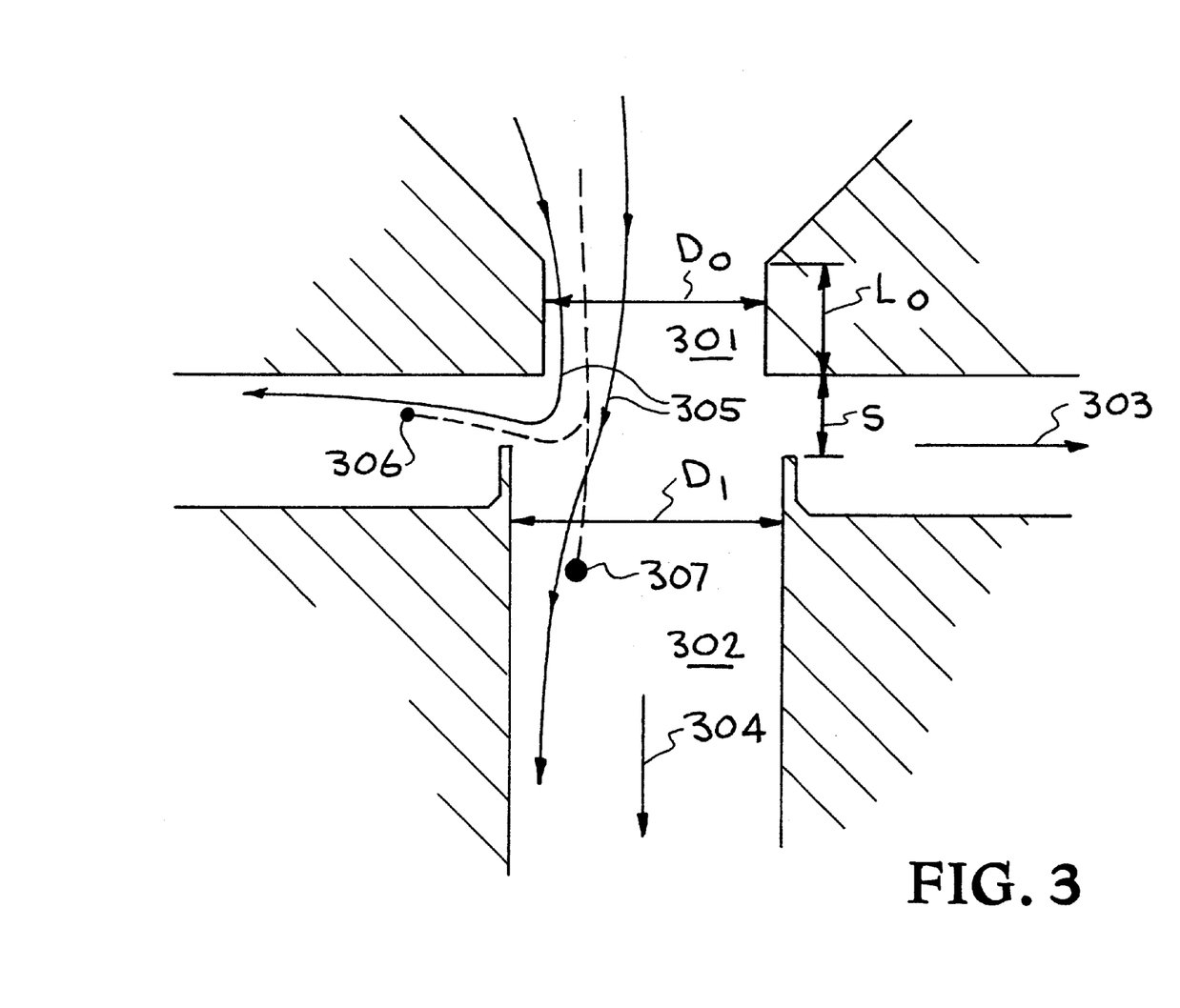
FIG. 3 is an illustration that shows the virtual impactor section.

Referring now to FIG. 3, the virtual impactor section 103 is shown wherein the separation efficiency is determined by the ratio of the major and minor flows (or Bypass to Product) and the physical dimensions of the nozzle and collection probe. The key is particulate larger than the cut size become concentrated in the minor flow. The concentration factor is the ratio of the total flow to the minor flow. (If the minor flow is 25% of the total flow, then the concentration factor is 4.) The aerosol passes through an acceleration nozzle 301 and is directed toward a collection probe 302 where a major portion of the flow 303 is diverted 90° away from it. The minor or "product" flow 304 continues axially.

The flow forms streamlines 305. Small particles with low inertia 306 follow the flow streamlines and are carried away radially with the major flow 303. Large particles with greater inertia 307 deviate from the flowlines but they continue moving axially in their forward path down the collection probe 302 with the minor or "product" flow 304. The separation efficiency is determined by the ratio of the major and minor flows (or Bypass to Product) and the physical dimensions of the nozzle $D_0$ and collection probe $D_1$. The key is particulate larger than the cut size become concentrated in the minor flow. The concentration factor is the ratio of the total flow to the minor flow.

Figure 4:
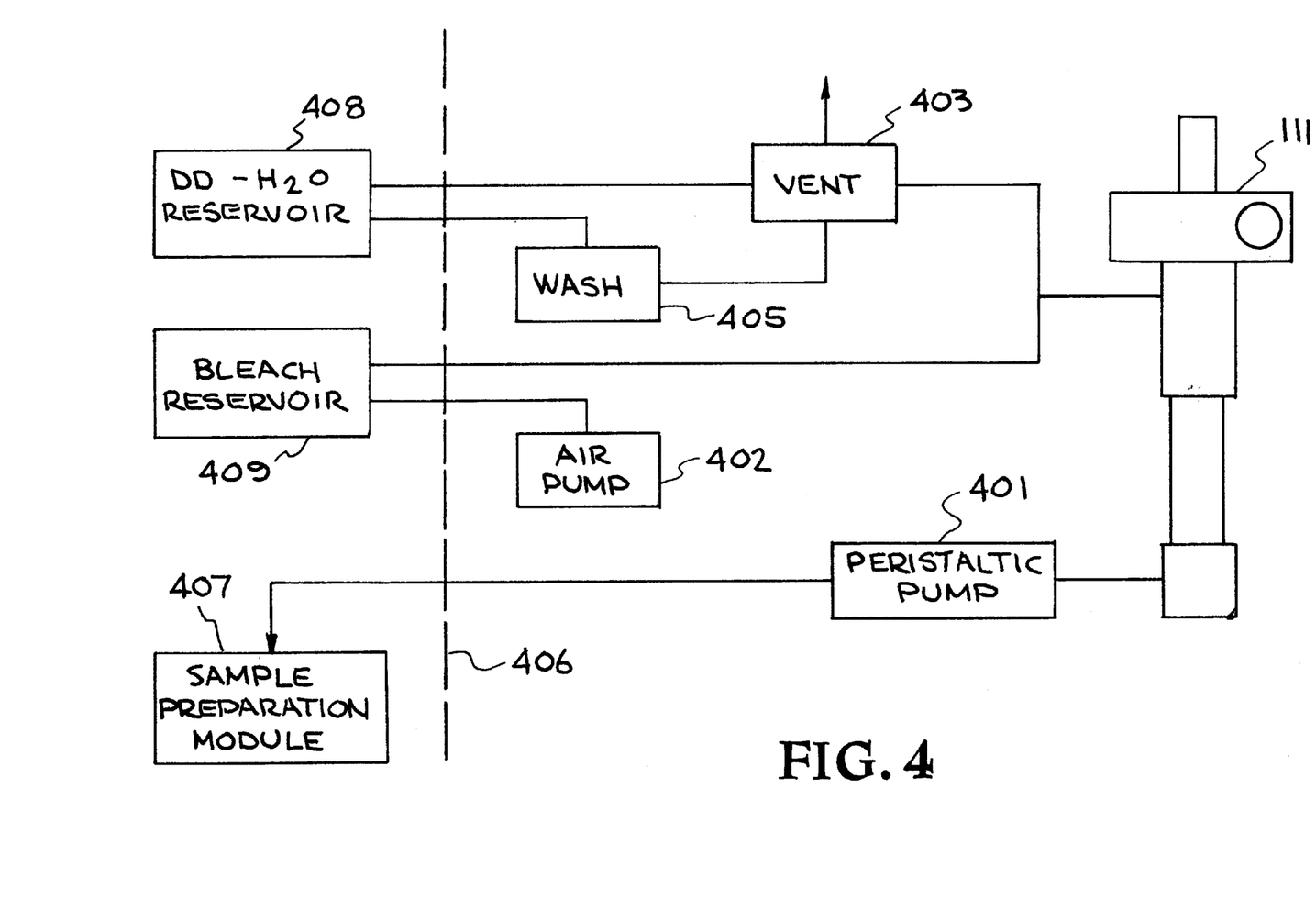
FIG. 4 shows the multistage, wetted-wall cyclone collector section.

Referring now to FIG. 4, the multistage, wetted-wall cyclone collector section 111 is shown. The particles (1–10 microns), called the product, flow down a stainless steel funnel section into the input of a multistage, wetted-wall cyclone collector 111. In this stage of the sampling system the product particles are trapped and concentrated into a liquid, typically water, in a volume between 2 and 7 cc.

The system includes a peristaltic pump 401, an air pump 402, a vent 403, fill 404, wash 405, 8 liter DD-H$^2$O reservoir 408, and 1 liter bleach reservoir 409. The reservoirs 408 and 409 are provided as external tanks outside of the front panel interface 406.

An on-board computer monitors and controls the flow of air through the system using built in hot wire anemometers that have been mounted in the two exhaust ports of the sampler. The computer and control software also act to control the liquid level in the cyclone, and monitor all status indicators of the sampling system. At a selected time the computer will stop the flow of air and turn on a built-in peristaltic pump to deliver the collected liquid sample via an external sample port. The system also has the capability to measure particle sizes in the background environment via a built in particle counter such as particle counter Biotest APC-1000, with four size ranges, and can store and display the results in real-time.

The system 100 is entirely self-contained requiring only a 110 vac power connection. The on-board computer has high-speed communications capability allowing networking of multiple sampling systems to be remotely operated. The computer has extra RS-232 or RS-485 serial ports that can be used to control other instrumentation. A keyboard, mouse, printer, displays, and other peripherals can be "plugged" in at the rear of the system, or it can be started "headless" (headless=Without a display, mouse, etc.)

Figure 5A:
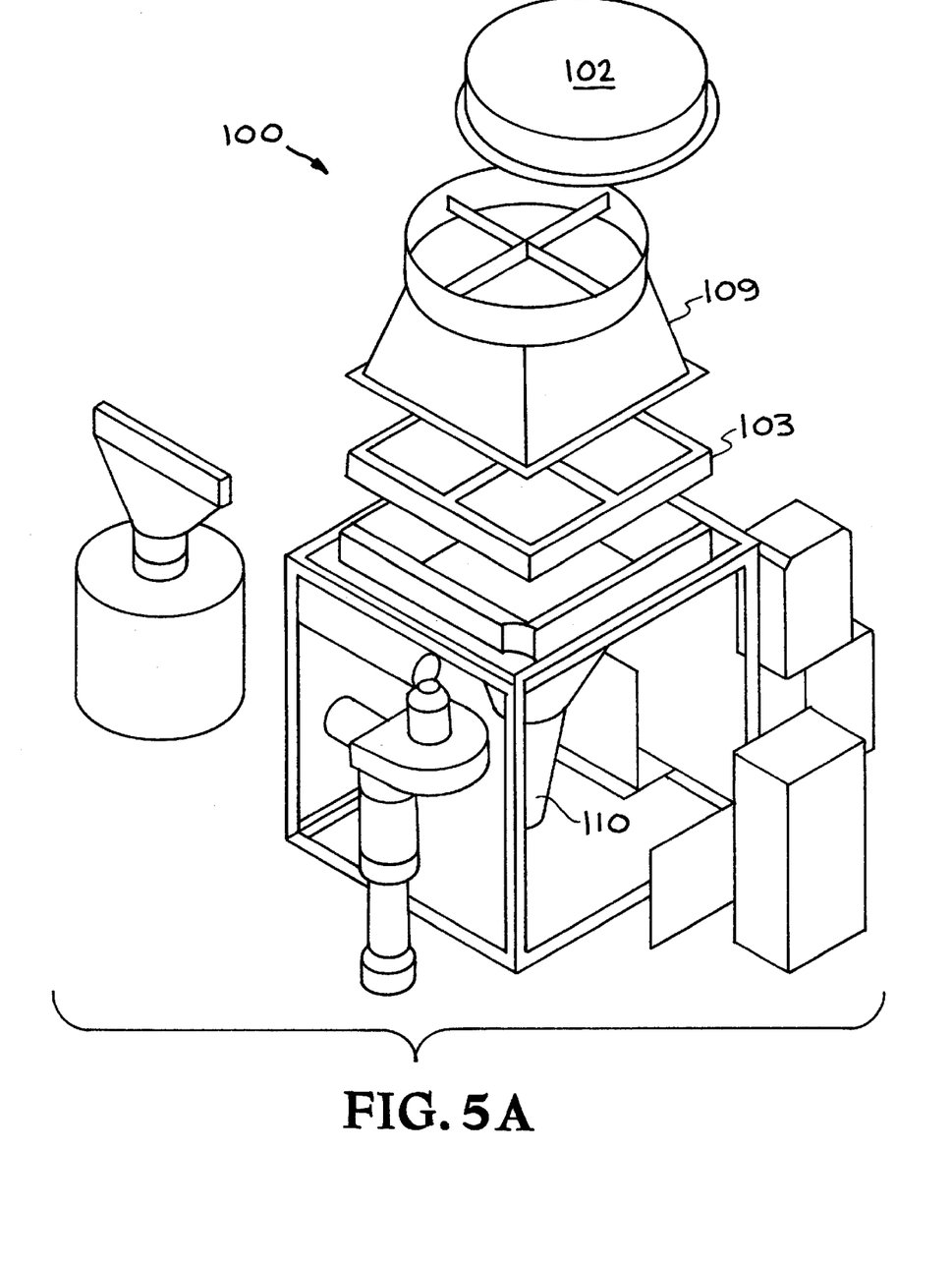
FIGS. 5A, 5B, and 5C show details of a specific embodiment of the invention designated the High Collection Rate Aerosol Sampling System (HiCRASS).
Figure 5B:
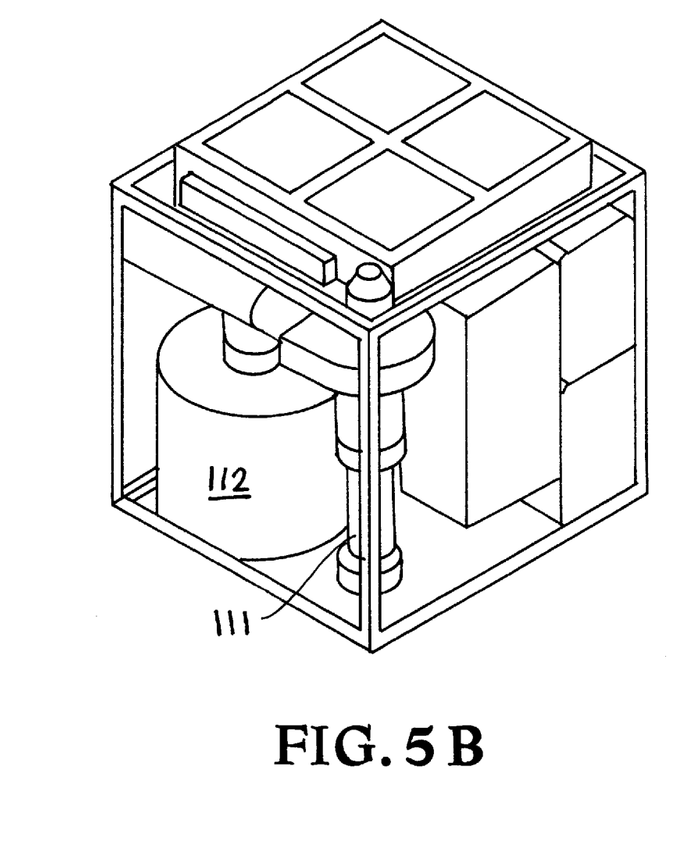
Figure 5C:
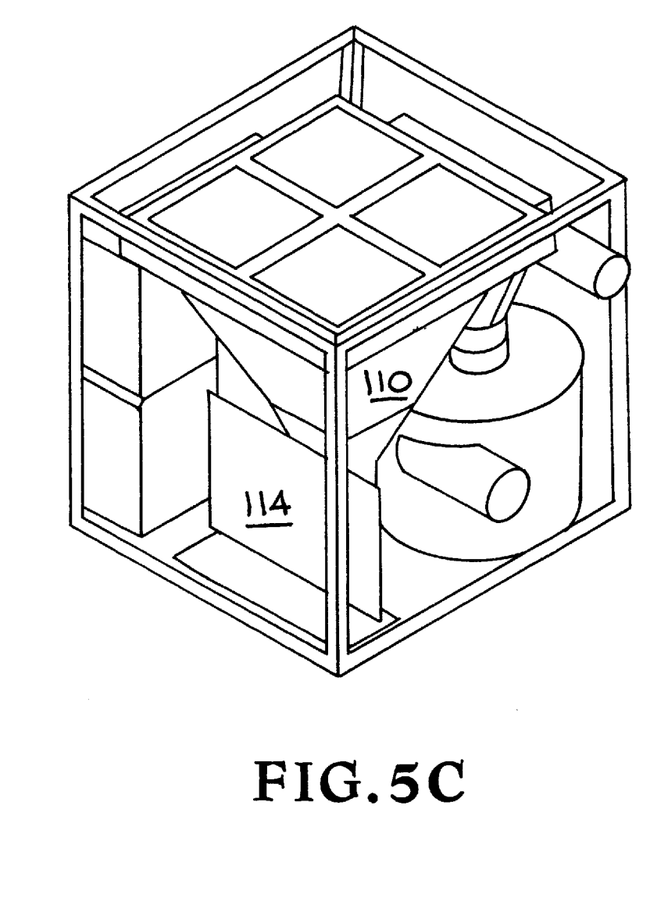

Referring now to FIGS. 5A, 5B, and 5C, the specific embodiment 100 is shown in greater detail. The specific embodiment 100 is designated as "High Collection Rate Aerosol Sampling System" (HiCRASS). The HiCRASS system 100 comprises: Low Pass "Cap" 102; Transition Section 109; Virtual Impactor 103; Funnel Section 110; Multistage, Wetted-wall Cyclone Collector 111; Bypass Fan 112; and Control Computer 114.

The HiCRASS system 100 provides a very high volume flow of aerosol particles (e.g., up to 3313 Lpm) that are drawn into the annular slot 101 (shown in FIGS. 1 and 2) formed in the cap 102 that is designed to limit the upper or larger particulate size range as they enter the collector. The annular slot 101 allows the passage of particles smaller than 10 microns. To efficiently pass the smaller particulate, the cap 102 is a "passive" device in that is has no moving parts and uses the fact that particulate with a finite mass and moving in a flowstream (in this case air) will not follow the streamlines exactly due to their inertia. The curvature of the streamline is sufficiently large and the mass of the particulate is correspondingly high that the particle deviates far enough from the streamline to impact with a surface. The accepted particles continue around the corner and onto the dichotomous virtual impaction section 103 that returns substantially all the aerosol particles smaller than 1-micron back into the environment.

The virtual impactor 103 (shown in greater detail in FIG. 3) works as the aerosol passes through an accelerating nozzle 301 and is directed toward a collection probe 302 where a major portion of the flow 303 is diverted 90° away from it. The flow forms streamlines 305. Small particles with low inertia 306 follow the flow streamlines and are carried away radially with the major flow 303. Large particles with greater inertia 307 deviate from the flowlines but they continue moving axially in their forward path down the collection probe 302 with the minor or "product" flow 304. The separation efficiency is determined by the ratio of the major and minor flows (or Bypass to Product) and the physical dimensions of the nozzle $D_0$ and collection probe $D_1$. The key is particulate larger than the cut size become concentrated in the minor flow. The concentration factor is the ratio of the total flow to the minor flow. (If the minor flow is 25% of the total flow, then the concentration factor is four (4).

The remaining particles (1–10 microns) now known as the product 304, flow down a stainless steel funnel section into the input of the multistage, wetted-wall cyclone collector section 111 (shown in FIG. 4). In this stage of the sampling system 100 the product particles are trapped and concentrated into a liquid, typically water, in a volume between 2 and 7 cc. The wetted-wall cyclone collector section 111 is a system that causes the product flow particles 304 to be collected by a liquid. The wetted-wall cyclone collector section 111 operates by forcing the air stream tangentially into the cylinder 111 causing the air stream to circulate around the inside of the cylinder 111. Particles in the air stream having sufficient inertia will collide with the interior wall where they are collected by the liquid that circulates along the interior wall.

The on-board computer 114 monitors and controls the flow of air through the system using built-in hot wire anemometers, as well as controlling the liquid level in the cyclone 111. At a selected time the computer 114 will stop the flow of air and turn on a built-in peristaltic pump to deliver the sample via an external sample port. The on-board computer 114 monitors and controls the flow of air through the system using built in hot wire anemometers that have been mounted in the two exhaust ports of the sampler. The computer and control software also act to control the liquid level in the cyclone, and monitor all status indicators of the sampling system. At a selected time the computer will stop the flow of air and turn on a built-in peristaltic pump to deliver the collected liquid sample via an external sample port.

The system also has the capability to measure particle sizes in the sampling environment via a built in particle counter such as particle counter Biotest APC-1000, with four size ranges, and can store and display the results in real-time. The system is entirely self-contained requiring only a 110 vac power connection. The on-board computer has high-speed communications capability allowing networks of these sampling systems to be remotely operated.

Figure 6:
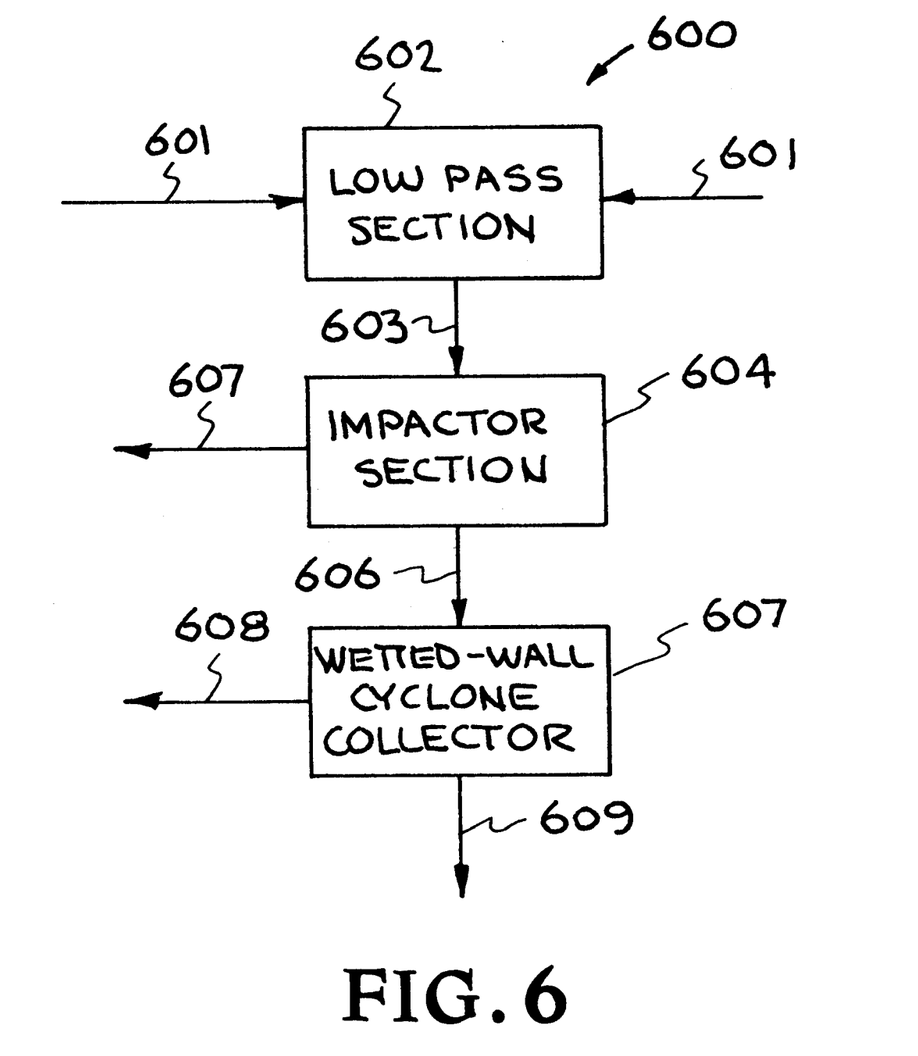
FIG. 6 illustrates another specific embodiment of the invention.

Referring now to FIG. 6, another specific embodiment of the invention is illustrated. This embodiment is designated generally by the reference numeral 600. The system 600 samples the air 601 and collects sample particles of a predetermined particle size range from the air. The system 600 is particularly useful with the latest generation of Biological Warfare agent detection systems. An air sampling system is a critical component in integrated biological warfare detection system. The system 600 also has use in medical facilities and research and development facilities.

A low pass section 602 has an opening of a preselected size for gathering the air 601 but excluding particles larger than the sample particles. In one embodiment, the opening of a preselected size is an annular slot that only allows the passage of particles smaller than 10 microns. The low pass section 602 produces a total air flow 603 that contains the sample particles of a predetermined particle size range. The low pass section 602 allows a very high volume flow of air to be drawn through the preselected size opening. In one embodiment, the very high volume flow of air is 3313 Lpm or less.

An impactor section 604 is connected to the low pass section 602 and receives the total air flow 603. The impactor section 604 separating the total air flow 603 into a bypass air flow 607 that does not contain the sample particles and a product air flow 606 that does contain the sample particles. An accelerating nozzle and a collection probe in the impactor section 604 diverts the bypass air flow 90° from the product air flow thereby separating the bypass air flow and the product air flow. In one embodiment, the bypass air flow and the product air flow separation is determined by the ratio of the bypass air flow and the product air flow. In one embodiment, the bypass air flow and the product air flow separation is determined by the physical dimensions of the accelerating nozzle and the collection probe. In one embodiment, the bypass air flow and the product air flow separation is determined by the ratio of the bypass air flow and the product air flow and the physical dimensions of the accelerating nozzle and the collection probe.

A wetted-wall cyclone collector section 607 is connected to the impactor section 604. The wetted-wall cyclone collector section 607 receives the product air flow 606 and traps the sample particles in a liquid. The sample particles of a predetermined particle size range are concentrated in the liquid. In one embodiment, the wetted-wall cyclone collector section 607 traps and concentrates the sample particles into a liquid in a volume between 2 and 7 cc. In one embodiment, the liquid is water.

The system 600 is useful for most environmental sampling. It is particularly useful with biological material collection, but can be used for collecting any airborne matter. The system 600 can be used to sample air quality in public buildings such as convention centers and sports arenas, for sampling in food processing facilities, sampling animal pens (such as poultry houses), or for use in monitoring orchards or agricultural areas for the presence of pollens or pesticides. Because of it's relatively compact size and weight it can be used to sample in confined spaces such as found in aircraft or subway systems.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for sampling air and collecting sample particles of a predetermined particle size range from said air, comprising:

a low pass section having an opening for gathering said air, an impactor section operatively connected to said low pass section, said impactor section receiving said air and separating said air into a bypass air flow that does not contain said sample particles and a product air flow that contains said sample particles, and a wetted-wall cyclone collector section operatively connected to said impactor section, said wetted-wall cyclone collector section receiving said product air flow and trapping and concentrating said sample particles.

2. The apparatus of claim 1 wherein said opening in said low pass section size is an annular slot.

3. The apparatus of claim 2 wherein said annular slot allows the passage of particles smaller than 10 microns.

4. The apparatus of claim 1 wherein said impactor section includes an acceleration nozzle and a collection probe operatively connected to separate said bypass air flow and said product air flow.

5. The apparatus of claim 4 wherein said acceleration nozzle and said collection probe are positioned where said bypass air flow is diverted 90° from said product air flow.

6. The apparatus of claim 4 wherein said acceleration nozzle and said collection probe provide separation of said bypass air flow and said product air flow and said separation is determined by the ratio of said bypass air flow and said product air flow.

7. The apparatus of claim 4 wherein said acceleration nozzle and said collection probe provide separation of said bypass air flow and said product air flow and said separation is determined by the physical dimensions of said accelerating nozzle and said collection probe.

8. The apparatus of claim 4 wherein said acceleration nozzle and said collection probe provide separation of said bypass air flow and said product air flow said separation is determined by the ratio of said bypass air flow and said product air flow and the physical dimensions of said accelerating nozzle and said collection probe.

9. The apparatus of claim 1 wherein said wetted-wall cyclone collector traps and concentrates said sample particles of a predetermined particle size range into a liquid in a volume between 2 and 7 cc.

10. The apparatus of claim 9 wherein said liquid is water.

* * * * *